United States Patent [19]

Höchstetter

[11] Patent Number: 5,258,511

[45] Date of Patent: Nov. 2, 1993

[54] PYRAZOLOAZEPINONES AND METHODS OF USING SUCH PYRAZOLOAZEPINONES TO DYE SYNTHETIC FIBERS AND TO PIGMENT PASTES, PAINTS, PRINTING INKS, COLORED PAPER AND COLORED MACROMOLECULAR SUBSTANCES

[75] Inventor: Hans Höchstetter, Duesseldorf, Fed. Rep. of Germany

[73] Assignee: Bayer Aktiengesellschaft, Leverkusen, Fed. Rep. of Germany

[21] Appl. No.: 918,157

[22] Filed: Jul. 20, 1992

Related U.S. Application Data

[63] Continuation of Ser. No. 808,971, Dec. 16, 1991, abandoned, which is a continuation of Ser. No. 488,580, Mar. 5, 1990, abandoned.

[30] Foreign Application Priority Data

Mar. 11, 1989 [DE] Fed. Rep. of Germany ....... 3908036
Mar. 23, 1989 [DE] Fed. Rep. of Germany ....... 3909595

[51] Int. Cl.$^5$ .................. C07D 487/04; C09B 57/00
[52] U.S. Cl. ................... 540/521; 540/577; 540/578; 548/359.5; 548/430; 8/662; 8/922
[58] Field of Search .......... 540/521, 578; 8/662, 8/922

[56] References Cited

U.S. PATENT DOCUMENTS

| | | | |
|---|---|---|---|
| 2,898,265 | 8/1959 | Wegler et al. | 514/608 |
| 2,903,451 | 9/1959 | Smith | 548/364 |
| 2,914,523 | 11/1959 | Grundmann et al. | 534/652 |
| 4,228,168 | 10/1980 | Sato et al. | 424/256 |
| 4,666,526 | 5/1987 | Rolf et al. | 544/245 |
| 4,743,615 | 5/1988 | Jelich et al. | 514/404 |
| 4,810,283 | 3/1989 | Gehring et al. | 71/92 |
| 4,909,827 | 3/1990 | Gehring et al. | 71/92 |

OTHER PUBLICATIONS

Sircar et al, *J. Heterocyclic Chem.*, 18, pp. 117-121, (1981).
Organic Syntheses, Collective vol. 4, pp. 34-38, (1967).
Beilsteins handbuch der organischen chemie vierte au- (List continued on next page.)

*Primary Examiner*—Mukund J. Shah
*Assistant Examiner*—Philip Datlow
*Attorney, Agent, or Firm*—Sprung Horn Kramer & Woods

[57] ABSTRACT

Heterocyclic compounds of the formula

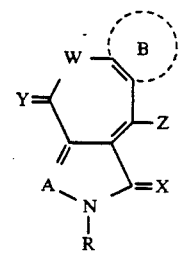

in which R represents hydrogen, substituted or unsubstituted alkyl, substituted or unsubstituted cycloalkyl, substituted or unsubstituted aryl, substituted or unsubstituted hetaryl, A represents C—$R^1$, N, $R^1$ represents substituted or unsubstituted alkyl, substituted or unsubstituted cycloalkyl, substituted or unsubstituted aryl, substituted or unsubstituted hetaryl, X, Y represent O, NH, Z represents hydrogen, —CN, substituted or unsubstituted aryl, substituted or unsubstituted hetaryl, W represents O, N—$R^5$, $R^5$ represents hydrogen, substituted or unsubstituted alkyl, substituted or unsubstituted cycloalkyl, substituted or unsubstituted aryl, a substituted or unsubstituted heterocyclic radical and B represents a substituted or unsubstituted carbocyclic-aromatic or heterocyclic ring onto which one or more further rings can be fused, and the use of these compounds as dyestuffs or pigments.

8 Claims, No Drawings

OTHER PUBLICATIONS flage die literatur bis 1. Jan. 1910 un 4th edition pp. 76-86 (1931).
Simpson et al., J. Chem. Soc., p. 646 (1945).
Bell et al., J. Chem. Soc., p. 3560 (1955).
Beilstein, II Ergänzungswerk p. 51 (1951).
Beilstein, III Ergänzungswerk, pp. 213, 214-216 (1973).
Beilstein, IV Ergänzungswerk, pp. 243, 245-247 (1985).
Gungor, J. Organometallic Chem., vol. 215, No. 2 PP. 139-150 (1981).
Bruyne, Pharm. Weekbl. Sci. Ed., vol. 4, No. 1 pp. 12-15 (1982).
Organic Chemistry, 4th Edition pp. 1273-1275 (1983) Boyd.
"Pyrazolones, Pyrazolidones and Derivatives", Richard H. Wiley, Paul Wiley, (1964), pp. 95-97.

PYRAZOLOAZEPINONES AND METHODS OF USING SUCH PYRAZOLOAZEPINONES TO DYE SYNTHETIC FIBERS AND TO PIGMENT PASTES, PAINTS, PRINTING INKS, COLORED PAPER AND COLORED MACROMOLECULAR SUBSTANCES

This application is a continuation of application Ser. No. 808,971, filed Dec. 16, 1991, now abandoned which is a continuation of Ser. No. 488,580 filed Mar. 5, 1990, now abandoned.

The invention relates to heterocyclic compounds of the formula (I)

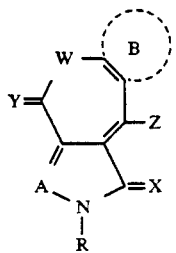

processes for their preparation and their use as dyestuffs or pigments, in particular for the dyeing or pigmenting of high-molecular weight organic material or as pigments for paints.

In formula (I),

R represents hydrogen, substitute or unsubstituted alkyl, substituted or unsubstituted cycloalkyl, substituted or unsubstituted aryl, substituted or unsubstituted hetaryl, A represents $C-R^1$ or N, $R^1$ represents substituted or unsubstituted alkyl, substituted or unsubstituted cycloalkyl, substituted or unsubstituted aryl, substituted or unsubstituted hetaryl, X, Y represent O, NH, Z represents hydrogen, —CN, substituted or unsubstituted aryl, substituted or unsubstituted hetaryl, W represents O, N—$R^5$, $R^5$ represents hydrogen, substituted or unsubstituted alkyl, substituted or unsubstituted cycloalkyl, substituted or unsubstituted aryl, a substituted or unsubstituted heterocyclic radical, B represents a substituted or unsubstituted carbocyclic-aromatic or heterocyclic ring onto which one or more further rings can be fused.

Alkyl (R, $R^1$) preferably represents $C_1-C_6$-alkyl, particularly preferably $C_1-C_4$-alkyl. Examples are: methyl, ethyl, n- and i-propyl, n-, i- and t-butyl.

Cycloalkyl (R, $R^1$) preferably represents mono-, bi- and tricyclic $C_3-C_{10}$-cycloalkyl, particularly preferably cyclopropyl, cyclopentyl, cyclohexyl.

The alkyl and cycloalkyl radicals (R, $R^1$, W) can be substituted, for example, by Cl, Br, F, —CN, —OH, $C_1-C_6$-alkoxy, mono-$C_1-C_4$-alkylamino, di-$C_1-C_4$-alkylamino, phenyl or naphthyl, which can be substituted by Cl, Br, F, $C_1-C_6$-alkyl and $C_1-C_6$-alkoxy or radicals of a 5- or 6-membered ring system containing 1 or 2 heteroatoms from the series consisting of O, N, S, onto which a benzene ring can be fused.

Aryl (R, $R^1$, Z) preferably represents those carbocyclic-aromatic radicals which contain 1, 2, 3 or 4, in particular 1 or 2, rings, for example phenyl, diphenyl and naphthyl.

Hetaryl (R, R:, Z) preferably represents those heterocyclic-aromatic radicals which contain 1, 2, 3 or 4, in particular 1 or 2, five-, six- or seven-membered rings, at least one of which contains 1, 2 or 3, preferably 1 or 2, heteroatoms from the series consisting of O, N, S.

Examples of heterocyclic-aromatic radicals are: pyridyl, pyrimidyl, pyrazinyl, triazinyl, furanyl, pyrrolyl, thienyl, quinolyl, coumarinyl, benzofuranyl, benzimidazolyl, benzoxazolyl, dibenzofuranyl, benzothienyl, dibenzothienyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, orthosulphobenzimidyl, maleimidyl, naphtharidinyl, benzimidazolonyl, benzoxazolonyl, benzothiazolonyl, benzothiazolinyl, quinazolonyl, pyrimidonyl, quinoxalonyl, phthalazonyl, dioxapyrimidinyl, pyridonyl, isoquinolonyl, isoquinolinyl, isothiazolyl, benzoisoxazolyl, benzoisothiazolyl, indazolonyl, acridinyl, acridonyl, quinazolinedionyl, quinoxalinedionyl, benzoxazinedionyl, benzoxazinonyl and naphthalimidyl.

The aryl and hetaryl radicals (R, $R^1$, Z) can be substituted, for example, by halogen, such as chlorine, bromine, fluorine, CN, $R^2$, $OR^3$, $SR^3$, $NR^5$, $R^6$, $COOR^7$, $NR^3COR^7$, $NR^3COOR^7$, $NR^3CONR^5R^6$, —$NHSO_2R^7$, —$SO_2R^7$, $SOR^7$, $SO_2OR^7$, $CONR^5R^6$, $SO_2NR^5R^6$, —N=N—$R^{10}$, $OCOR^7$ and $OCONHR^7$.

$R^2$ represents substituted or unsubstituted alkyl, in particular $C_1-C_6$-alkyl, particularly preferably $C_1-C_4$-alkyl. Examples of substituents are: Cl, Br, F, —CN, —$OCOR^7$, —$OR^3$, —$COOR^7$, —$SR^3$, —$CONR^5R^6$, —$OCONHR^7$.

$R^5$ and $R^6$ represent hydrogen, substituted or unsubstituted alkyl, in particular $C_1-C_{18}$-alkyl, preferably $C_1-C_4$-alkyl, substituted or unsubstituted cycloalkyl, in particular cyclopentyl and cyclohexyl, substituted or unsubstituted aryl, in particular phenyl, naphthyl and diphenylyl, and a substituted or unsubstituted heterocyclic radical, in particular the radical of a 5- or 6-membered heterocyclic ring containing 1, 2 or 3 heteroatoms from the series consisting of 0, N, S, onto which a benzene ring can be fused.

The alkyl and cycloalkyl radicals $R^5$ and $R^6$ can be substituted, for example, by Cl, Br, F, —CN, —OH, mono-$C_1-C_4$-alkylamino, di-$C_1-C_4$-alkylamino, phenyl or naphthyl, which can be substituted by Cl, Br, F, $C_1-C_6$-alkyl and $C_1-C_6$-alkoxy or heterocyclic radicals of a 5- or 6-membered heterocyclic ring system which contains 1 or 2 heteroatoms from the series consisting of O, N, S, onto which a benzene ring can be fused.

It is also possible for $R^5$ and $R^6$ in the group —$CONR^5R^6$ to form a 5- or 6-membered heterocyclic ring together with the N atom, for example a morpholine or piperidine ring.

The aryl and aralkyl radicals $R^5$ and $R^6$ can be substituted, for example, by Cl, Br, F, $C_1-C_{18}$-alkyl, preferably $C_1-C_4$-alkyl, $C_1-C_{18}$-alkoxy, preferably $C_1-C_4$-alkoxy.

$R^7$ represents hydrogen, substituted or unsubstituted alkyl, preferably $C_1-C_4$-alkyl, substituted or unsubstituted cycloalkyl, in particular cyclopentyl and cyclohexyl, substituted or unsubstituted aralkyl, in particular phenyl- and naphthyl-$C_1-C_4$-alkyl, preferably benzyl, substituted or unsubstituted aryl, in particular phenyl and naphthyl, and a substituted or unsubstituted heterocyclic radical, in particular the radical of a 5- or 6-membered ring containing 1, 2 or 3 heteroatoms from the series consisting of O, N, S, onto which a benzene ring can be fused.

The radicals mentioned for $R^7$ can be substituted, for example, in the same way as the corresponding radicals $R^5$ and $R^6$.

$R^3$ represents hydrogen or adopts the meanings of $R^5$.

$R^{10}$ represents the radical of a coupling component, preferably a coupling component from the benzene, naphthalene, pyrazole or pyridone series or a phenyl radical which is unsubstituted or substituted by Cl, Br, F, $C_1$-$C_4$-alkyl or $C_1$-$C_4$-alkoxy.

The ring B in formula (I) can be an aromatic or heteroaromatic ring of the type mentioned for aryl (R, $R^1$, Z) or hetaryl (R, $R^1$, Z) which can carry, in addition to the two substituents at the bridging points

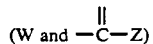

(W and —C—Z)

the substituents mentioned above for substituted aryl and hetaryl.

Furthermore, B can also represent a non-aromatic heterocyclic radical which contains 1, 2, 3 or 4, in particular 1 or 2, five-, six- or seven-membered rings, at least one of which contains 1, 2, 3 or 4, preferably 1 or 2, heteroatoms from the series consisting of O, N, S. These heterocyclic radicals B can in turn be substituted by substituted or unsubstituted aryl or hetaryl which have the abovementioned meaning.

Particularly preferred rings B are substituted or unsubstituted aromatics having the abovementioned meaning and the substituted pyrazole, pyridine or pyrimidine derivatives (briding points indicated by W and C-Z) or their tautomeric forms shown below.

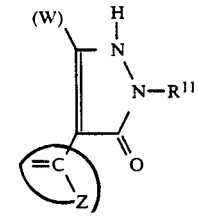

(II)

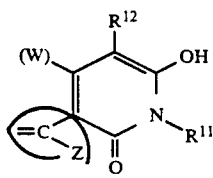

(III)

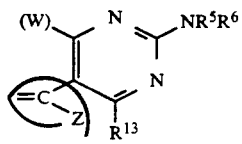

(IV)

In formulae (II), (III) and (IV), $R^{11}$ represents an aromatic or heteroaromatic radical of the abovementioned meaning having the abovementioned substitution (see R, $R^1$, Z), $R^{12}$ represents —CN, —COOR$^7$, —CONR$^5$R$^6$ in which $R^5$, $R^6$ and $R^7$ have the abovementioned meaning, $R^{13}$ represents halogen or OR$^3$ in which $R^3$ has the above-mentioned meaning.

The substituents $R^5$ and $R^6$ in formula (IV) also have the abovementioned meaning.

Preferred compounds according to the invention are those of the formula (I) in which W is N—R$^5$ in which $R^5$ has the abovementioned meaning, X, Y are O, Z is H, —CN, substituted or unsubstituted aryl, A is N, C-alkyl, which can be substituted, C-aryl, which can be substituted, and B is a substituted aromatic ring, substituted pyrazole, pyrimidine or pyridine ring.

Compounds which in one of their tautomeric forms correspond to the formulae Va-Vd are particularly preferred.

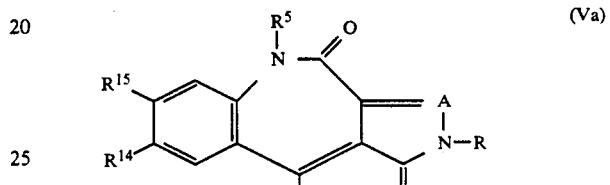

(Va)

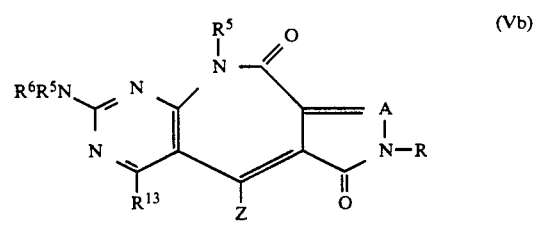

(Vb)

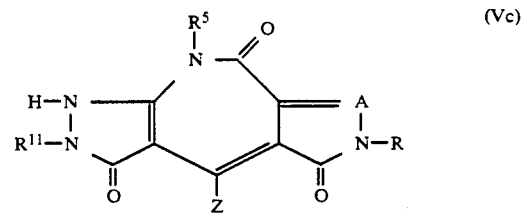

(Vc)

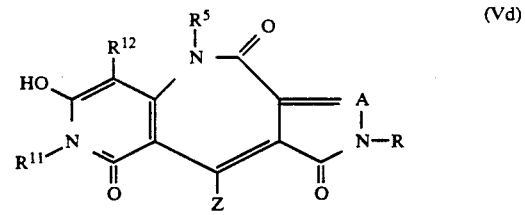

(Vd)

In these formulae the radicals R, A, $R^5$, $R^6$, $R^{13}$, $R^{11}$, $R^{12}$ and Z have the abovementioned meanings;

Particularly preferably,

R represents phenyl, which can be substituted by 1 or 2 substituents from the series consisting of —SO$_3$H, halogen (Cl, Br), —CN, $C_1$-$C_4$-alkyl, —SO$_2$NH$_2$.

Apart from N, A particularly preferably represents

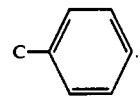

$R^{14}$, $R^{15}$ represent hydrogen, halogen, $OR^3$ or $NR^5R^6$ in which $R^3$, $R^5$ and $R^6$ have the meanings mentioned.

The compounds of the formula I in which Z is H are obtained by reacting either aldehydes of the formula

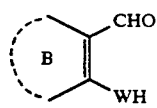 (VI)

(or their functional derivatives, for example their Schiff's bases) in which B and W have the abovementioned meanings with compounds of the formula

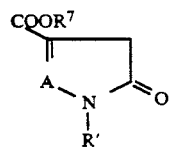 (VII)

in which R, $R^7$ and A have the abovementioned meanings or by reacting formylated derivatives (which may be protected in the form of an anil) of (VII), that is compounds of the type

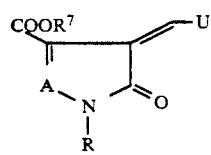 (VIII)

with acidic C-H heterocycles of the type

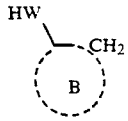 (IX)

(IX) can be present in various tautomeric forms.

In the formulae (VIII) and (IX), U denotes $OR^3$ or $NHR^5$, $R^3$, $R^5$, $R^7$ and R' have the above-mentioned meanings.

W and B also have the abovementioned meanings, B preferably representing heterocyclic rings.

The C-H acidity of the $CH_2$ group in formula (IX), as a result of suitable substitution in the ring B, must be such that it can react with the aldehyde group (or its equivalent) in (VIII).

The reactions mentioned can go through intermediates which rearrange with proton migration(s) to give a tautomeric form of the formula (I).

The reaction is advantageously carried out under the known conditions of the Knoevenagel condensation, that is, in a suitable solvent in the presence of an acid or basic catalyst. Suitable solvents are alcohols, glycols, aromatic hydrocarbons and aliphatic carboxylic acids and their amides.

Suitable acid catalysts are carboxylic acids, sulphonic acids and aminoacids, suitable basic catalysts are aliphatic amines. If the aldehyde (VI) or (VIII) used is the corresponding anil (Schiff's base), the addition of a catalyst can be omitted when the reaction is carried out in alcohols or carboxylic acids.

The reaction temperatures are between 20° and 150° C., preferably between 80° and 130° C.

The reaction to give (I) comprises two steps, namely condensation of an aldehyde (or aldehyde equivalent) with an active methylene group and intramolecular esterification or lactam formation (=reaction of the group —WH with the group $CO_2R^7$), which, however, are carried out in a one-pot reaction. Isolation of an intermediate or primary product is not required or even not feasible.

The preparation of compounds of the formula (I) in which Z is CN is carried out, for example, by reacting compounds of the formula (I) in which Z is H in a polar solvent such as dimethylformamide with cyanide salts and employing an oxidizing agent simultaneously or afterwards. This type of reactions is known in principle (cf. DE-A 2,844,299, U.S. Pat. Nos. 4,609,738, 4,634,779, 4,547,579, and 4,550,171.

Suitable cyanide salts are NaCN and KCN, suitable oxidizing agents are peroxides, persulphates, halogens, lead tetraacetate and nitric acid.

The reaction with the cyanides is carried out at 0°-120° C., preferably at 10°-40° C.

The oxidation is carried out at 0°-20° C.

Compounds of the formula (I) in which Z is aryl or hetaryl and W is NH are prepared by reacting β-aminoketones of the type

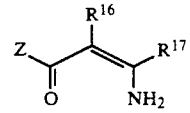 (X)

in which
Z is a substituted or unsubstituted aromatic or heteroaromatic and
$R^{16}$ and $R^{17}$ together represent the radicals of a fused-on substituted or unsubstituted aromatic or heteroaromatic with an azolecarboxylic acid derivative of the type (VII).

The β-aminoketones of the formula (X) are known. See, for example, H. J. Scheifele Jr. Et al., Org. Synth. Coll., Vol. 4, p. 34–38 (1967); Simpson et al., J. Chem. Soc., p. 646 (1945); Bell et al., J. Chem. Soc., p. 3560 (1955); Beilstein, 4th Edition, p. 76 (1931); Beilstein, II. Ergänzungswerk, p. 51 (1951); Beilstein, III. Ergänzungswerk, p. 213, 214–216 (1973); Beilstein, IV. Ergänzungswerk, p. 243, 245–247 (1985); J. Organometallic Chem., Vol. 215, No. 2, pp. 139–150 (1981); and Pharm. Weekbl., Sci. Ed., Vol. 4, No. 1, pp. 12–15 (1982).

Compounds of the formula (I) in which W is N-alkyl are prepared by reacting compounds of the type I in which W is NH in a dipolar aprotic solvent such as dimethylformamide in the presence of a non-nucleophilic base such as potassium carbonate or sodium carbonate with alkyl tosylates as N-alkylating agent. These reactions are also known in principle from the literature [e.g. H. Langhals, T. Potrawa, Chem. Ber. 120, 1075 (1987)].

The aldehydes (VI) in which WH is OH or NH₂ and which are used as starting material are known or easily accessible by conventional methods. Carbocyclic derivatives are described, for example, in DE-A-2,415,661, DE-A 1,098,125 U.S. Pat. No. 3,014,091 and U.S. Pat. No. 5,052,678 and DE-A 2,363,548.

Other aldehydes are easily accessible from halogenated nitrobenzaldehydes known from the literature. Heterocyclic representatives of (VI) are, for example, accessible from aminouracil derivatives by Vilsmeier formylation (K. Hirota et al., Synthesis 1984, 589).

A large number of azolecarboxylic acid derivatives of the type (VII) are also known and readily accessible. Pyrrole derivatives are described, for example, in EP-A 0,184,981 US. Pat. No. 4,681,971 and U.S. Pat. No. 4,769,795. Pyrazoles derivatives are accessible by the Japp-Klingemann reaction of diazotized amines with acetosuccinic esters in a wide range of substitution patterns (R. Heckendorn, Bull. Soc. Chim. Belg. 95 (1986), 921).

The components (VIII) are accessible from azole precursors (VII) by reaction with orthoesters [e.g. O. Wolfbeis, Mn. Chem. 112, 369 (1981)].

As components (IX), almost any desired heterocycle which contains the group WH defined above in more detail and an acidic C-H methylene group in a suitable position can be used.

The new substances of the formula (I) are dyestuffs or pigments and are suitable, depending on the substitution, either for the dyeing of synthetic fibres in yellow to violet hues or for their use as pigments in yellow to red hues for paints or plastics. Some dyestuffs have very good heat stability and can be used for the mass coloration of plastics.

The compounds of the formula (I) in which $Z \neq CN$, W is NH and X, Y are O are yellow to red substances and are preferably used as pigments, but, depending on their structure and the type of the polymer to be dyed, they can also be used as polymer-soluble dyestuffs for, for example, polystyrene, polyamides, ABS, in particular for linear polyesters, in particular polyethylene terephthalates. The compounds of the formula (I) are obtained in a form which is suitable for pigment application or can be converted into such a suitable form by after-treatment processes known per se, for example by dissolving or swelling them in strong inorganic acids such as sulphuric acid and pouring them onto ice. They can be finely divided by milling them with or without milling auxiliaries such as inorganic salts or sand, if desired in the presence of solvents such as toluene, xylene, dichlorobenzene or N-methylpyrrolidone. Colour strength and transparency of the pigment can be affected by varying the after-treatment.

By virtue of their light and migration fastness, the compounds of the formula (I) are suitable for a wide range of pigment applications. Thus, they can be used for the preparation of systems of very high pigment fastness in a mixture with other substances, preparations, paints, printing inks, coloured paper and coloured macromolecular substances. A mixture with other substances can be understood to mean, for example, those with inorganic white pigments such as titanium dioxide (rutile) or with cement. Preparations are, for example, flush pastes containing organic liquids or pastes and fine pastes with water, dispersions and, if desired, preservatives. The name paints denotes, for example, physically or oxidatively drying lacquers, stoving enamels, reaction lacquers, two-component lacquers, disperse paints for weatherproof-coatings and distempers. Printing inks are meant to mean those for paper, textile and tinplate printing. The macromolecular substances can be of natural origin such as rubber, be obtained by chemical modification such as acetylcellulose, cellulose butyrate or viscose or produced synthetically such as polymers, polyaddition products and polycondensation products. Examples are plastic materials such as polyvinyl chloride, polyvinyl acetate, polyvinyl propionate, polyolefins, for example polyethylene or polyamides, superpolyamides, polymers and mixed polymers of acrylic esters, methacrylic esters, acrylonitrile, acrylamide, butadiene, styrene and polyurethanes and polycarbonates. The substances which are pigmented by means of the claimed products can be present in any desired form.

The compounds of the formula (I) in which Z is H, CN and W is O and N-alkyl are highly suitable for the dyeing of synthetic fibres of, for example, aromatic polyesters or cellulose triacetate which can be dyed in yellow to violet hues to give dyeings which have good general fastness properties.

EXAMPLES

In the examples which follow, parts are by weight.

EXAMPLE 1

9 parts of 1-(2,4-dichlorophenyl)-3-ethoxycarbonyl-5-pyrazolone and 11 parts of o-aminobenzaldehyde protected by means of p-toluidine are refluxed in 300 parts of glacial acetic acid for 5.5 hours. The mixture is filtered off with suction while hot, and the product is washed with glacial acetic acid and methanol until the filtrate remains colourless. This gives 14 parts of the compound.

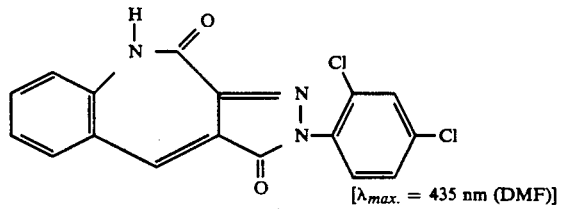

$[\lambda_{max.} = 435 \text{ nm (DMF)}]$

The procedure of Example 1 is repeated, using appropriately substituted pyrazolone esters and aminobenzaldehyde equivalents to give the pigments and dyestuffs of the formula (XI) listed in the table below

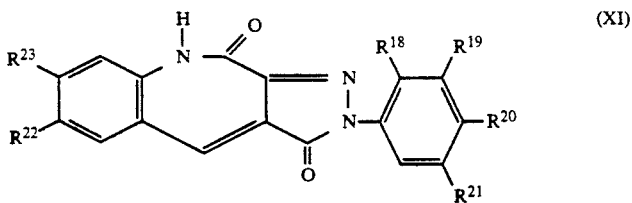

| Ex. | R$^{18}$ | R$^{19}$ | R$^{20}$ | R$^{21}$ | R$^{22}$ | R$^{23}$ | Yield | $\lambda_{max}$ | [nm] (DMF) |
|---|---|---|---|---|---|---|---|---|---|
| 1 | Cl | H | Cl | H | Cl | H | 78 | 440 | |
| 3 | Cl | H | H | Cl | Cl | H | 51 | 464 | |
| 4 | H | H | Cl | H | Cl | H | 74 | 458 | |
| 5 | H | H | Br | H | H | H | 84 | 447 | |
| 6 | H | H | Cl | H | H | H | 89 | | |
| 7 | H | H | Br | H | Cl | H | 76 | | |
| 8 | Cl | H | H | Cl | H | H | 72 | 436 | |
| 9 | H | CN | CN | H | H | NMe$_2$ | 80 | 484, | 506 |
| 10 | H | H | t-Butyl | H | H | NEt$_2$ | 66 | 490 | |
| 11 | H | H | Cl | H | H | NMe$_2$ | 60 | 486 | |
| 12 | H | H | SO$_2$NH$_2$ | H | H | H | 91 | 442 | |

The procedure of Example 1 is repeated, using pyrrolone derivatives instead of pyrazolone derivatives, to give pyrroloazepinones (orange pigments) for which Example 13 is representative.

EXAMPLE 13

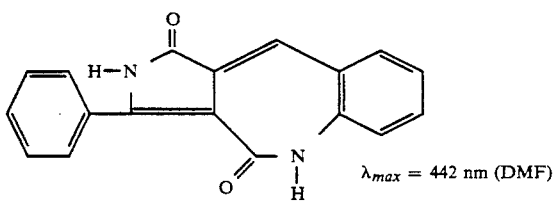

$\lambda_{max}$ = 442 nm (DMF)

Those representatives of the formula (I) which carry a six-membered heterocycle as ring B are represented by Example 14.

EXAMPLE 14

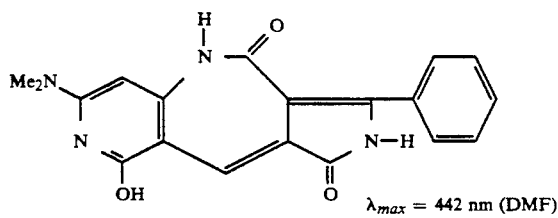

$\lambda_{max}$ = 442 nm (DMF)

If the reaction described in Example 1 is carried out in an aqueous-alcoholic solvent, it is also possible to use sulpho-containing pyrazolone derivatives, which leads to water-soluble dyestuffs, for which Example 15 is representative.

EXAMPLE 15 dyes wool and polyamide in a clear orange shade

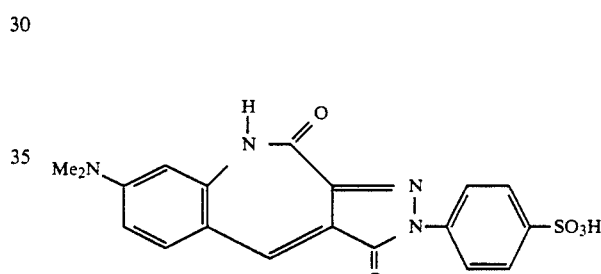

EXAMPLE 16

17 parts of the compound

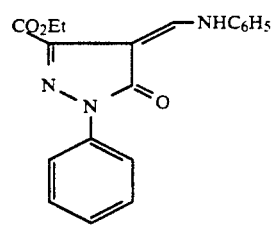

are refluxed with 9 parts of the compound

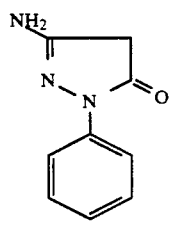

in 100 ml of glacial acetic acid for 18 hours. 11 parts of the compound

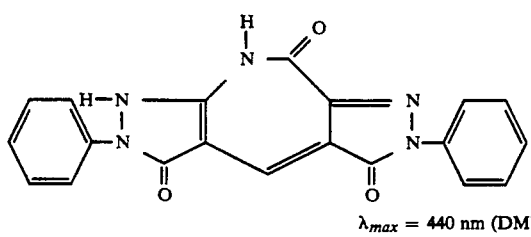

$\lambda_{max}$ = 440 nm (DMF)

are isolated.

EXAMPLE 17 (Working Example)

4 g of finely ground pigment according to Example 6 are dispersed in 92 g of a stoving enamel of the following composition:
- 33% of alkyd resin
- 15% of melamine resin
- 5% of glycol monomethyl ether
- 34% of xylene
- 13% of butanol Suitable alkyd resins are products based on synthetic and vegetable fatty acids such as coconut oil, castor oil, castor oil, ricinene oil, linseed oil and the like. Instead of melamine resins, it is also possible to use urea resins.

After the pigmented lacquer has been dispersed, it is applied to paper, glass, plastic or metal sheets and stoved at 130° C. for 30 minutes. The coatings have very good light and weather fastness and good overcoating fastness.

EXAMPLE 18 (Working Example)

0.2 g of the pigment according to Example 6 are mixed with 100 g of polyethylene, polypropylene or polystyrene granules. The mixture can either be moulded directly at 220° to 280° C. in an injection moulding machine or processed in an extruder to give coloured rods or on mixing rolls to give coloured sheets. If necessary, the rods and sheets are granulated and moulded in an injection-moulding machine.

The orange mouldings have very good light and migration fastness. It is also possible to colour synthetic polyamides of caprolactam or adipic acid and hexamethylenediamine or the condensation products of terephthalic acid with ethylene glycol in a similar manner at 280°-300° C., if necessary under a nitrogen atmosphere.

I claim:

1. A heterocyclic compound of the formula:

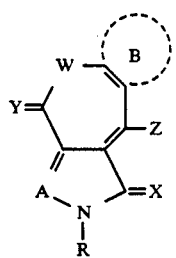

(I)

in which

R represents hydrogen, unsubstituted or substituted alkyl, unsubstituted or substituted cycloalkyl, unsubstituted or substituted aryl, or unsubstituted or substituted hetaryl, hetaryl being selected from the group consisting of pyridyl, pyrimidyl, pyrazinyl, triazinyl, furanyl, pyrrolyl, thienyl, quinolyl, coumarinyl, benzofuranyl, benzimidazolyl, benzoxazolyl, dibenzofuranyl, benzothienyl, dibenzothienyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, ortho-sulphobenzimidyl, maleimidyl, naphtharidyinyl, benzimidazolonyl, benzoxazolonyl, benzothiazolonyl, benzothiazolinyl, quinazolonyl, pyrimidonyl, quinoxalonyl, phthalazonyl, dioxapyrimidinyl, pyridonlyl, isoquinolonyl, isoquinolinyl, benzoisoxazolyl, benzoisothiazolyl, indazolonyl, acridinyl, acridonyl, quniazolinedionyl, quinoxalinedionyl, benzoxazinedionyl, benzoxazinonyl, and naphththalimidyl;

A represents N;

X, Y independently represent O or NH;

Z represents hydrogen, —CN, or unsubstituted or substituted aryl;

W represents N—$R^5$;

$R^5$ represents hydrogen, unsubstituted or substituted alkyl, unsubstituted or substituted cycloalkyl, or unsubstituted or substituted aryl;

B represents an unsubstituted or substituted carbocyclic aromatic ring onto which one or more further rings can be fused.

$R^1$ represents unsubstituted or substituted aryl, or unsubstituted or substituted hetaryl, hetaryl being selected from the group consisting of pyridyl, pyrimidyl, pyrazinyl, triazinyl, furanyl, pyrrolyl, thienyl, quinolyl, coumarinyl, benzofuranyl, benzimidazolyl, benzoxazolyl, dibenzofuranyl, benzothienyl, dibenzothienyl, indolyl, carbazolyl, pyrazolyl, imidazolyl, oxazolyl, isoxazolyl, thiazolyl, indazolyl, benzothiazolyl, pyridazinyl, cinnolyl, quinazolyl, quinoxalyl, phthalazinyl, phthalazinedionyl, phthalimidyl, chromonyl, naphtholactamyl, benzopyridonyl, ortho-sulphobenzimidyl, maleimidyl, naphtharidinyl, benzimidazolonyl, benzoxazolonyl, benzothiazolonyl, benzothiazolinyl, quinazolonyl, pyrimidonyl, quinoxalonyl, phthalazonyl, dixapyrimidinyl, pyridonyl, isoquinolonyl, isoquinolinyl, isothiazolyl, benzoisoxazolyl, benziothiazolyl, indazolonyl, acridinyl, acridonyl, quinazolinedionyl, quinoxalinedionyl, benzoxazinedionyl, benzoxazinonyl, and naphthalimidyl;

$R^{12}$ represents —CN, —COO$R^7$, —CONR$^5$R$^6$;

$R^6$ represents hydrogen, unsubstituted or substituted alkyl, unsubstituted or substituted cycloalkyl, or unsubstituted or substituted aryl;

$R^7$ represents hydrogen, unsubstituted or substituted alkyl, unsubstituted or substituted cycloalkyl, unsubstituted or substituted aralkyl, or unsubstituted or substituted aryl;

$R^{13}$ represents halogen or —OR$^3$; and $R^3$ represents hydrogen, unsubstituted or substituted alkyl, unsubstituted or substituted cycloalkyl, or unsubstituted or substituted aryl.

2. A compound according to claim 1, wherein B represents an unsubstituted or substituted carbocyclic aromatic ring.

3. Compounds according to claim 1 in which X, Y are O, W is N—$R^5$, Z is H, —CN, substituted or unsubstituted aryl, A is N, and B is a substituted aromatic ring.

4. Compounds according to claim 1 in one of their tautomeric forms which correspond to the formula

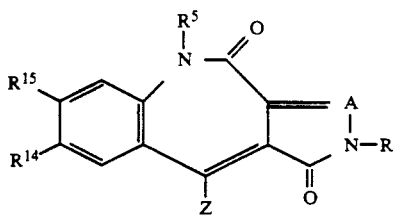
(Va)

in which $R^{14}$, $R^{15}$ represent hydrogen, halogen, $OR^3$, $NR^5R^6$, $R^3$ represents hydrogen or has the meanings mentioned for $R^5$ and $R^6$ has the meanings mentioned for $R^5$.

5. Compounds according to claim 1 in which R represents phenyl which can be substituted by 1 or 2 substituents from the series consisting of $-SO_3H$, halogen, $-CN$, $C_1$-$C_4$-alkyl, $-SO_2NH_2$.

6. A method of dyeing synthetic fibres comprising dyeing the synthetic fibres with a heterocyclic compound of the formula (I) according to claim 1.

7. A method of pigmenting pastes, paints, printing inks, colored paper and colored macromolecular substances comprising admixing therein a heterocyclic compound of the formula (I) according to claim 1.

8. The method according to claim 7, wherein in the heterocyclic compound Z is not $-CN$, W is $N-H$ and X, Y are O.

* * * * *